United States Patent
Harada et al.

(10) Patent No.: US 7,718,393 B2
(45) Date of Patent: May 18, 2010

(54) METHOD FOR DETERMINING THE EFFICACY OF AN ANTHRACYCLINE ANTICANCER AGENT

(75) Inventors: Amane Harada, Fort Lee, NJ (US); Tomokazu Yoshida, Kobe (JP)

(73) Assignee: Sysmex Corporation, Kobe-shi (JP)

( * ) Notice: Subject to any disclaimer, the term of this patent is extended or adjusted under 35 U.S.C. 154(b) by 53 days.

(21) Appl. No.: 11/939,138

(22) Filed: Nov. 13, 2007

(65) Prior Publication Data

US 2008/0124750 A1 May 29, 2008

(30) Foreign Application Priority Data

Nov. 13, 2006 (JP) .............................. 2006-307276

(51) Int. Cl.
*C12Q 1/02* (2006.01)
(52) U.S. Cl. ........................................................ 435/29
(58) Field of Classification Search .................... 435/29
See application file for complete search history.

(56) References Cited

U.S. PATENT DOCUMENTS

2005/0106639 A1* 5/2005 Bacus et al. ................. 435/7.2
2006/0294604 A1* 12/2006 Fridman et al. ............... 800/14

OTHER PUBLICATIONS

Li X. et al. Differential Responses to Doxorubicin Induced Phosphorylation and Activation of Akt in Human Breast Cancer Cells. Breast Cancer Research 7:R589-R597, May 34, 2005.*
West, K. Activation of the PI3K/Akt Pathway and Chemotherapeutic Resistance. Drug Resistance Updates 5:234-248, 2002.*
Jonas Cicenas et al., Increased level of phosphorylated akt measured by chemiluminescence-linked immunosorbent assay is a predictor of poor prognosis in primary breast cancer overexpressing ErbB-2, Breast Cancer Research, 2005, pp. R394-R401, vol. 7, No. 3.
Kim et al, "The role of apoptotic or nonapoptotic cell death in determining cellular response to anticancer treatment", European Journal of Surgical Oncology, London, GB, vol. 32, No. 3, Apr. 2006, pp. 269-277.

Cicenas J. et al, "Increased Level of Phosphorylated Akt Measured by Chemiluminescence-Linked Immunosorbent Assay is a Predictor of Poor Prognosis in Primary Breast Cancer Overexpressing ERBB-2" Breast Cancer Research, Current Science, London, GB, vol. 7, No. 4, Mar. 24, 2005, pp. R394-R401.
Fujiwara et al, "Inhibition of the PI3 kinase/Akt pathway enhances doxorubicin-induced apoptotic cell death in tumor cells in a p53-dependent manner" Biochemical and Biophysical Research Communications, Academic Press Inc. Orlando, FL, US, vol. 340, No. 2, Feb. 10, 2006, pp. 560-566.
Li Xinqun et al, "Differential response to doxorubicin-induced phosphorylation and activation of Akt in human breast cancer cells" Breast Cancer Research, Current Science, London, GB, vol. 7, No. 5, May 24, 2005, pp. R589-R597.
Clark A S et al, "Constitutive and Inducible Akt Activity Promotes Resistance to Chemotherapy, Trastuzumab, or Tamoxifen in Breast Cancer Cells" Molecular Cancer Therapeutics, American Association of Cancer Research, US, vol. 1, No. 9, Jul. 2002, pp. 707-717.
West K A et al, "Activation of the PI3K/Akt pathway and chemotherapeutic resistance" Drug Resistance Updates, Churchill Livingstone, Edinburgh, GB, vol. 5, No. 6, Dec. 2002, pp. 234-248.
Database Biosis [Online] Biosciences Information Service, Philadelphia, PA, US; Sep. 2005, Wan Xiao-Yun et al: "Sensitivity of PTEN gene-transfected endometrial carcinoma cell line to doxorubicin-induced apoptosis" XP002467525 Database accession No. PREV200600120180 & Zhonghua Zhongliu Zazhi, vol. 27, No. 9, Sep. 2005, pp. 513-515.

* cited by examiner

*Primary Examiner*—Ralph Gitomer
(74) *Attorney, Agent, or Firm*—Sughrue Mion, PLLC

(57) ABSTRACT

The present invention provides a method for determining susceptibility to an anthracycline anticancer agent, comprising the steps consisting of detecting the expression of activated Akt in a cancer cell or cancer tissue and determining the susceptibility of the cancer cell or cancer tissue to the anthracycline anticancer agent on the basis of the detection result. The method for determining the susceptibility to an anticancer agent can be used in objective and accurate determination of the susceptibility of a cancer cell or cancer tissue to an anthracycline anticancer agent without imposing a heavy burden on a patient.

7 Claims, 15 Drawing Sheets

METHOD FOR DETERMINING THE EFFICACY OF AN ANTHRACYCLINE ANTICANCER AGENT

FIELD OF THE INVENTION

The present invention relates to a method for determining the efficacy of an anthracycline anticancer agent and a device therefor.

BACKGROUND

As one of general therapies for cancer, there is chemotherapy. In chemotherapy, various kinds of anticancer agents are administered. However, effective anticancer agents vary depending on the type of cancer and patient's individual difference. Further, there are many cases wherein an anticancer agent, there is overlap between therapeutic range and maleficent range. Accordingly, there is a danger that the possibility of cancer recurrence is increased when an ineffective anticancer agent is administered. In addition, a patient's strength is lowered by administration of an ineffective anticancer agent. Therefore, there is a danger that even if another effective anticancer agent is then administered to the patient, its efficacy cannot be sufficiently demonstrated. From the foregoing, there is demand for development of a device for predicting drug responsiveness to specify an effective anticancer agent accurately prior to administration in order to secure safety and attain effectiveness.

Conventionally, a method which comprises contacting various anticancer agents with cancer cells or cancer tissues isolated from a patient, and on the basis of growth suppression etc. of the cancer cells as the indicator, specifying an anticancer agent estimated to be effective against the cancer cells has been used in examination of the sensitivity of anticancer agents to cancer. However, there are cases where examination results of such trial-and-error method are not sufficiently indicative of clinical effects. In addition, large amounts of cancer cells or cancer tissues are necessary in the test of anticancer agents, so there is a problem of great burden on patients. Accordingly, there is desire for establishment of a more objective and accurate method for determining the susceptibility of a cancer to anticancer agents.

It has been confirmed that serine-threonine kinase Akt is activated in many cancer tissues. It has also been suggested that Akt is closely related to malignant transformation. Activation of Akt requires phosphorylation. Activated Akt promotes phosphorylation of molecules involved in suppression of cell death. Cellular apotosis is thereby suppressed and cellular malignant transformation is caused. It is reported that patients with overexpression of activated Akt, as compared with those with underexpression of activated Akt, are generally at an increased risk for worse progress after operation and for adverse prognosis (Cicenas et al., Breast Cancer Research, Vol. 7, No. 3, pp. 394-401 (2005)). Generally, chemotherapy with anticancer agents is poor in efficacy for adverse-prognosis cancer. Accordingly, adverse-prognosis cancer is hardly treated. As a result, a patient with adverse-prognosis cancer is at high risk for cancer recurrence.

An anthracycline anticancer agent is an anticancer agent which inhibits recombination of DNA for topoisomerase II, thereby inducing apotosis. The anthracycline anticancer agent is clinically highly valued. Particularly, it is widely used in chemotherapy for breast cancer. However, the anthracycline anticancer agent, similar to other anticancer agents, might cause significant side effects such as cardiac toxicity and reduction in white blood cell. Accordingly, it is very important to establish an objective and accurate method for determining the susceptibility of cancers to the anthracycline anticancer agent.

SUMMARY

The scope of the present invention is defined solely by the appended claims, and is not affected to any degree by the statements within this summary.

Under these circumstances, the present inventors made extensive study for achieving a method for determining the susceptibility of a cancer cell or cancer tissue collected from a patient, to an anthracycline anticancer agent. As a result, they found the following i) to vii) to arrive at completion of the present invention:

i) a cancer cell or cancer tissue with overexpression of activated Akt is highly susceptible to an anthracycline anticancer agent;

ii) a cancer cell or cancer tissue with underexpression of activated Akt is low susceptible to an anthracycline anticancer agent;

iii) administration of an anthracycline anticancer agent is highly efficacious for cancer patients with overexpression of activated Akt;

iv) administration of an anthracycline anticancer agent is low efficacious for cancer patients with underexpression of activated Akt;

vi) a cancer cell or cancer tissue with overexpression of activated Akt and also with overexpression of human epidermal growth factor receptor 2 (HER-2) and/or PTEN is extremely highly susceptible to an anthracycline anticancer agent; and vii) a cancer cell or cancer tissue with underexpression of activated Akt and also with underexpression of HER-2 and/or PTEN is extremely low susceptible to an anthracycline anticancer agent.

That is, the present invention provides:

(1) a method for determining the efficacy of an anthracycline anticancer agent to a patient, comprising the steps of:
   detecting the expression of activated Akt in a cancer cell or cancer tissue collected from a patient, and
   determining the efficacy of the anthracycline anticancer agent to the patient on the basis of the detection result;

(2) the method according to the above-mentioned (1), wherein the cancer cell or cancer tissue is a cancer cell or cancer tissue of lung cancer, stomach cancer, colon cancer, ovarian cancer, brain cancer, breast cancer, prostate cancer, skin cancer or leukemia;

(3) the method according to the above-mentioned (1) or (2), wherein the cancer cell or cancer tumor is a cancer cell or cancer tissue of breast cancer;

(4) the method according to any of the above-mentioned (1) to (3), wherein the anthracycline anticancer agent is daunorubicin, doxorubicin, pirarubicin, aclarubicin, epirubicin, oxaunomycin or idarubicin;

(5) the method according to any of the above-mentioned (1) to (4), wherein the anthracycline anticancer agent is doxorubicin or epirubicin;

(6) the method according to any of the above-mentioned (1) to (5), which further comprises detecting the expression of human epidermal growth factor receptor 2 (HER-2) in the cancer cell or cancer tissue;

(7) the method according to any of the above-mentioned (1) to (6), which further comprises detecting the expression of PTEN in the cancer cell or cancer tissue;

(8) a device for determining the efficacy of an anthracycline anticancer agent to a patient, comprising:
an input part for entering the expression level of activated Akt in a cancer cell or cancer tissue collected from a patient,
a comparison part for comparing the entered expression level to a threshold level,
a determination part for determining the susceptibility of a cancer cell or cancer tissue to the anthracycline anticancer agent, on the basis of the comparison result, and an output part for outputting the determination result;

(9) the device according to the above-mentioned (8), wherein the cancer cell or cancer tissue is a cancer cell or cancer tissue of lung cancer, stomach cancer, colon cancer, ovarian cancer, brain cancer, breast cancer, prostate cancer, skin cancer or leukemia;

(10) the device according to the above-mentioned (8) or (9), wherein the cancer cell or cancer tumor a cancer cell or cancer tissue of breast cancer;

(11) the device according to any of the above-mentioned (8) to (10), wherein the expression level of human epidermal growth factor receptor 2 (HER-2) in the cancer cell or cancer tissue is further entered to the input part; and

(12) the device according to any of the above-mentioned (8) to (11), wherein the expression level of PTEN in the cancer cell or cancer tissue is further entered to the input part.

According to the present invention, there can be provided an objective and accurate method for determining the susceptibility of a cancer cell or cancer tissue to an anthracycline anticancer agent without imposing a heavy burden on patients, as well as a device therefor.

When the susceptibility of cancer cells or cancer tissues collected from patients to an anthracycline anticancer agent can be determined, the efficacy of the anthracycline anticancer agent to the individual cancer patients can be determined. According to the present invention, therefore, there can be provided a method for determining the efficacy of an anthracycline anticancer agent to a patient, as well as a device therefor.

Administration of an effective anthracycline anticancer agent is made feasible by using the present invention. Further, administration of an unnecessary anthracycline anticancer agent can be avoided to reduce a side-effect burden on patients.

DETAILED DESCRIPTION OF THE EMBODIMENT

Figure 1:
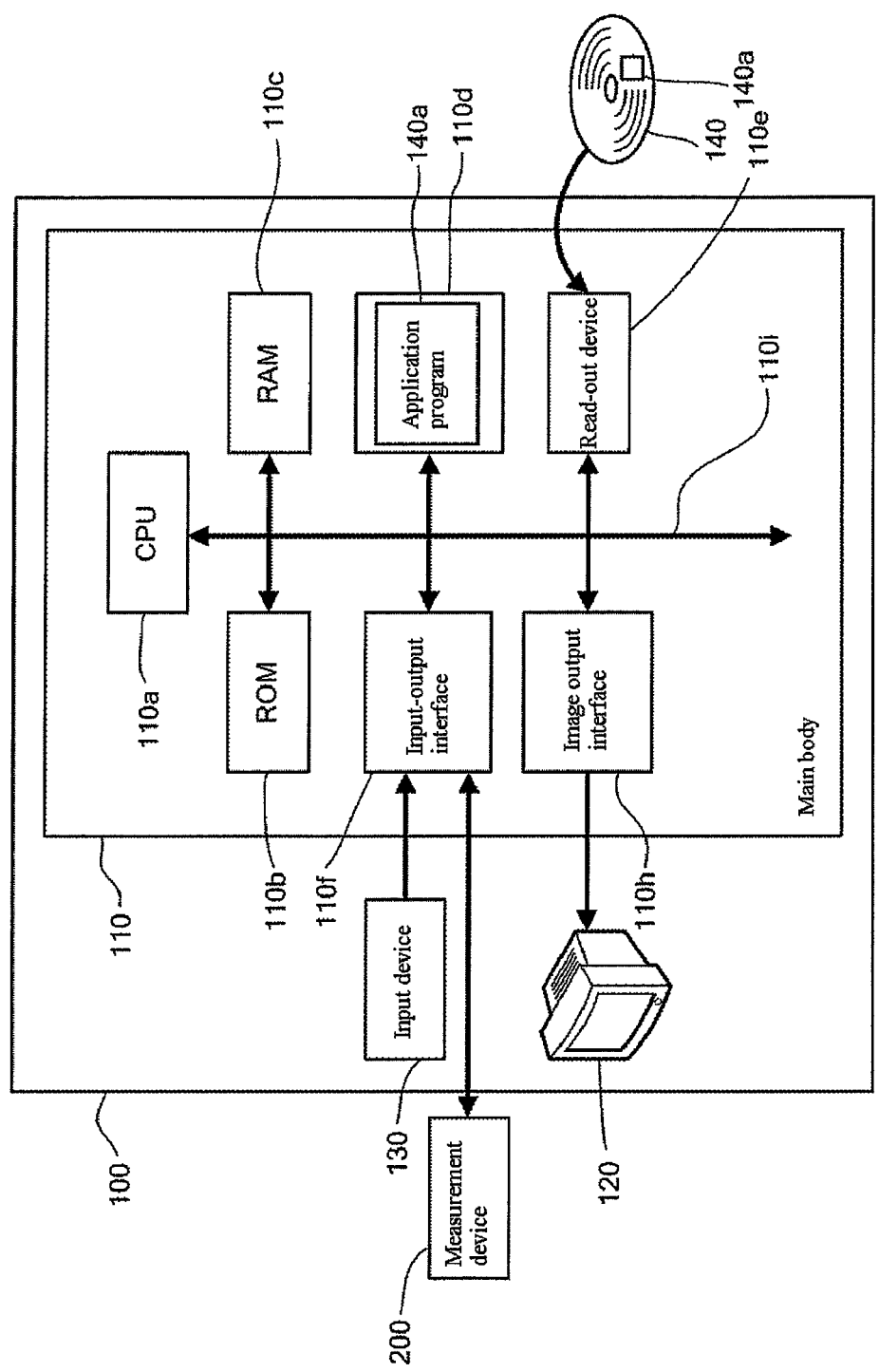
FIG. 1 shows one embodiment by a computer device of a device for determining susceptibility to an anticancer agent.

The cancer cell or cancer tissue in the present invention is not particularly limited. Specific examples include cancer cells or cancer tissues of lung cancer, stomach cancer, colon cancer, ovarian cancer, brain cancer, breast cancer, prostate cancer, skin cancer and leukemia. Particularly, a cancer cell or cancer tissue of breast cancer is preferable. Clinically, the cancer cell or cancer tissue used may be a cancer cell or cancer tissue collected from a cancer patient and is not particularly limited. Examples of such cancer cell or tissue include cancer cells or cancer tissues collected from cancer patients with lung cancer, stomach cancer, colon cancer, ovarian cancer, brain cancer, breast cancer, prostate cancer, skin cancer and leukemia. Particularly, a cancer cell or tissue collected from a patient with breast cancer is preferable.

Activated Akt in the present invention refers to phosphorylated Akt. The activated Akt refers particularly to Akt phosphorylated at 2 amino acid residues, that is, threonine 308 and serine 473.

The anthracycline anticancer agent in the present invention is not particularly limited insofar as it is an anthracycline-based compound having an anticancer action. Preferable examples include clinically used anthracycline antibiotics and derivatives thereof. Specific examples include daunorubicin, doxorubicin, pirarubicin, aclarubicin, epirubicin, oxaunomycin and idarubicin. Doxorubicin and epirubicin are particularly preferable.

The method of detecting the expression of activated Akt in the present invention is not particularly limited insofar as the occurrence or degree of expression of activated Akt can be confirmed. The detection method includes, for example, known protein detection methods. Specific examples include SDS polyacrylamide electrophoresis, two-dimensional electrophoresis, analysis using protein chips, enzyme-linked immunosorbent assay (ELISA), immunofluorescence, western blotting, dot blotting and immunoprecipitation.

The method of detecting the expression of HER-2 and PTEN according to the present invention is not particularly limited insofar as the occurrence or degree of expression of HER-2 and PTEN can be confirmed. It is possible to use, for example, known mRNA detection methods besides the above-mentioned protein detection methods. The known mRNA detection methods include, for example, RT-PCR, northern blotting, NASBA, and methods using DNA chips.

The expression of activated Akt, HER-2 and PTEN, when detected for confirming the occurrence or degree of expression thereof, may be directly confirmed with eyes etc. The expression level of activated Akt, HER-2 and PTEN can be measured and confirmed by numerical values etc.

The expression of activated Akt, HER-2 and PTEN, when measured for their expression level, can be determined by known methods of measuring protein or mRNA expression levels. For example, when western blotting is used, a result of western blotting is scanned with an image scanner. Then, the signal intensity of each band assigned to activated Akt, HER-2 and PTEN protein is analyzed. On the basis of the analysis result of signal intensity, the expression levels of activated Akt, HER-2 and PTEN proteins are determined. The measuring instrument is generally commercially available.

The threshold value in the present invention refers to a standard for determining the occurrence or degree of expression of activated Akt, HER-2 and PTEN in a cancer cell or cancer tissue as an object of determination, thereby determining the susceptibility of the cancer cell or cancer tissue to an anthracycline anticancer agent. Specific examples of the threshold value include the expression level of activated Akt etc. in a cell or tissue used as a control, the expression level of a housekeeping gene or a certain protein, and a cutoff value.

The step of determining susceptibility to an anthracycline anticancer agent in the present invention is not particularly limited insofar as the occurrence or degree of activated Akt can be determined from a detection result thereof. From the viewpoint of objectivity, it is preferable that the expression level of activated Akt is measured, and on the basis of the measurement result, the susceptibility to an anthracycline anticancer agent is determined.

The step of determining the susceptibility to an anthracycline anticancer agent in the present invention can also be carried out by measuring the occurrence and degree of activated Akt only. When the detection result of expression of HER-2 and/or PTEN is added to the determination step, the susceptibility to an anthracycline anticancer agent can be more accurately determined. From the viewpoint of objectivity, it is more preferable that the expression levels of HER-2 and PTEN are measured in the same manner as in detection of activated Akt, and on the basis of the measurement results, the susceptibility to an anthracycline anticancer agent is determined.

When the expression levels of activated Akt, HER-2 and PTEN in a cancer cell or cancer tissue as the object of determination are measured, the measurement results of their expression levels are compared absolutely or relatively with a threshold value as standard or with the expression levels of activated Akt, HER-2 and PTEN in a control sample, whereby the occurrence or degree of expression thereof can be determined. Examples of such method can include the following methods i) to iv):

i) a method wherein protein contents, nucleic acid contents, etc., in a cancer cell or cancer tissue sample as the object of determination and in a control sample are previously made even; then, the expression levels of activated Akt, HER-2 and PTEN in each sample are measured; then, the measurement results of the respective samples are compared with each other; and finally, the occurrence and degree of expression of activated Akt, HER-2 and PTEN are determined on the basis of the comparison results.

ii) a method wherein the expression levels of activated Akt, HER-2 and PTEN in a cancer cell or cancer tissue sample as the object of determination and in a control sample are measured; then the obtained measurement results are corrected with the protein content, nucleic acid content etc. in each of the samples used in measurement; then, the measurement results of the respective samples after correction are compared with each other; and finally, the occurrence and degree of expression of activated Akt, HER-2 and PTEN are determined on the basis of the comparison results.

iii) a method wherein a suitable housekeeping gene mRNA or a certain protein (for example, β-actin, glyceraldehyde-3-phosphate dehydrogenase or the like) is determined as an internal standard; then, the expression level of the internal standard and the expression level of activated Akt, HER-2 and PTEN, in a cancer cell or cancer tissue as the object of determination, are measured; then, the measurement results of the expression levels of the internal standard and activated Akt, HER-2 and PTEN are compared with each other; and finally, the occurrence and degree of expression of activated Akt, HER-2 and PTEN are determined on the basis of the comparison results.

iv) a method wherein the expression levels of activated Akt, HER-2 and PTEN in a plurality of cancer cells or cancer tissues different in susceptibility to an anthracycline anticancer agent are previously measured; from the accumulated measurement results, a threshold value for determining the occurrence and degree of expression levels of activated Akt, HER-2 and PTEN is established; and measurement results of the expression levels of activated Akt, HER-2 and PTEN in a cancer cell or cancer tissue as the object of determination are compared with the threshold value, thereby determining the occurrence and degree of expression of activated Akt, HER-2 and PTEN.

The device for determining susceptibility to an anticancer agent according to the present invention is performed preferably with a computer. Hereinafter, a determination device (FIG. 1) in one embodiment for carrying out the method for determining susceptibility to an anticancer agent according to the present invention, and a determination flow (FIG. 2) therefor, are described in detail.

The determination device 100 shown in FIG. 1 includes a computer main body 110, an input device 130 for entering necessary data to the computer main body 110, and a display 120 for displaying input-output data etc. The determination device 100 can further include an external recording medium 140 as necessary. A program 140a in this embodiment may be recorded on the external recording medium 140. Alternatively, the program 140a may be stored in memories 110b to 110d installed in the computer main body 110. CPU 110a, memories 110b to 110d, an input-output interface 110f, an image output interface 110h, and a read-out device 110e are connected to one another via bath 110i in the computer main body 110 such that data can be transmitted and received.

Figure 2:
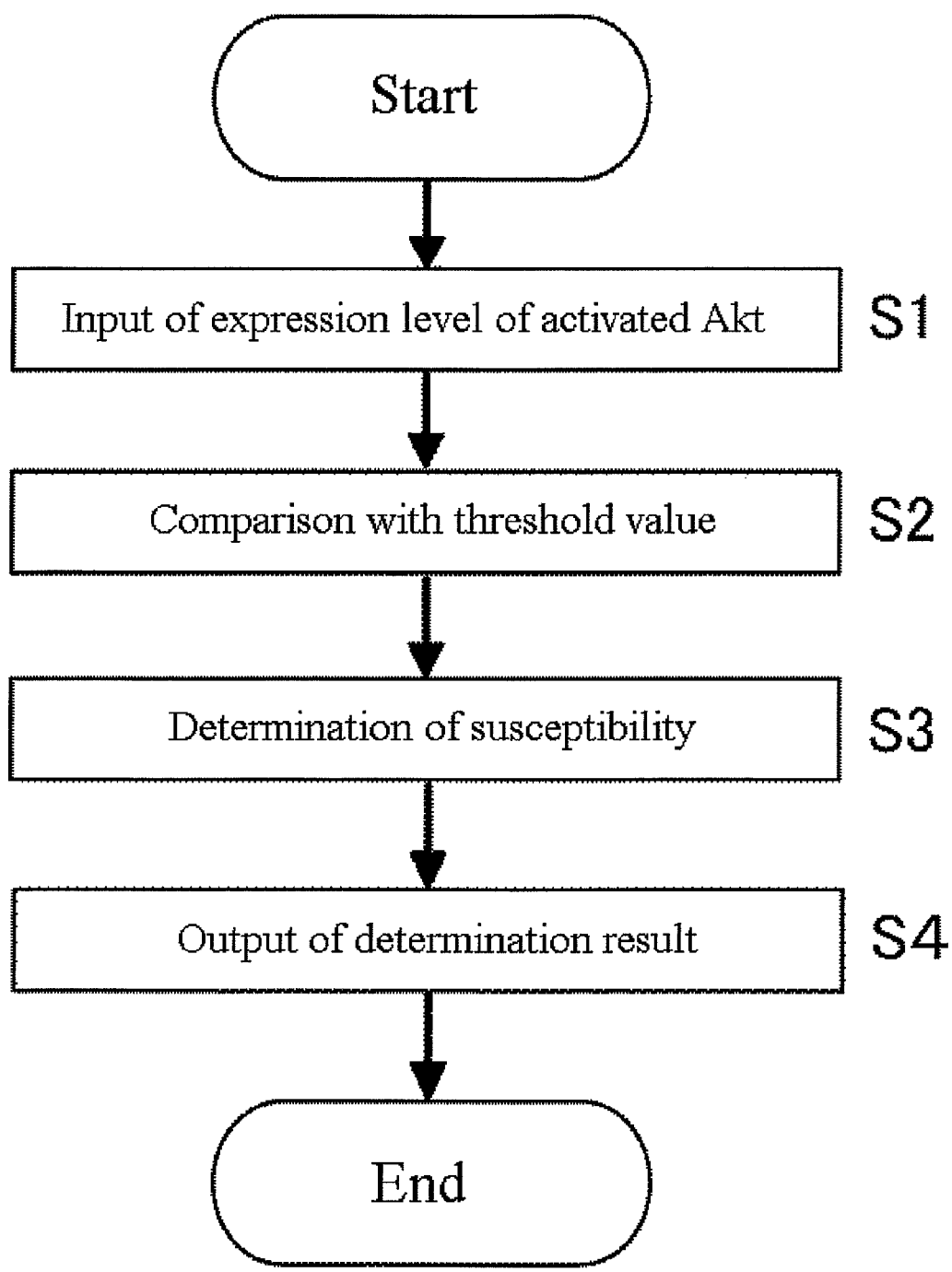
FIG. 2 shows a determination flow with a computer device of a device for determining susceptibility to an anticancer agent.
Figure 3:
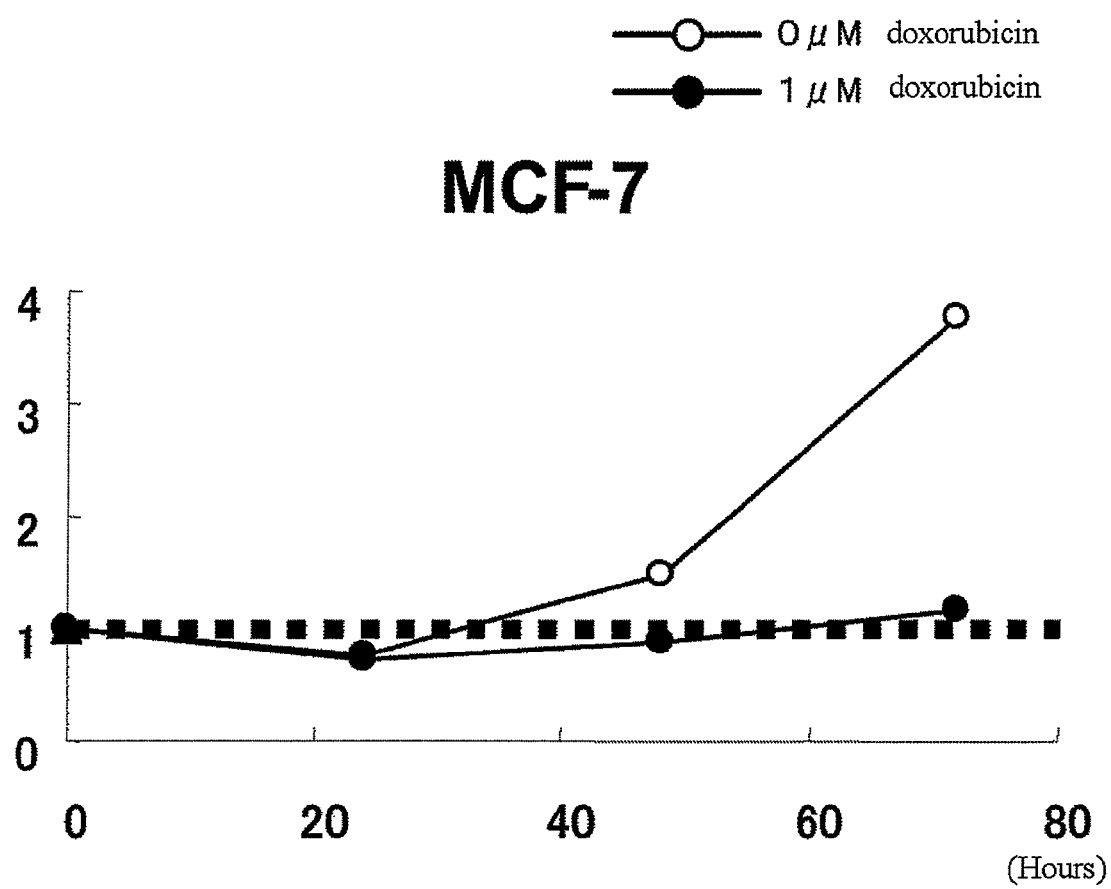
FIG. 3 shows the results of a cell growth test of MCF-7 in the presence or absence of doxorubicin.
Figure 4:
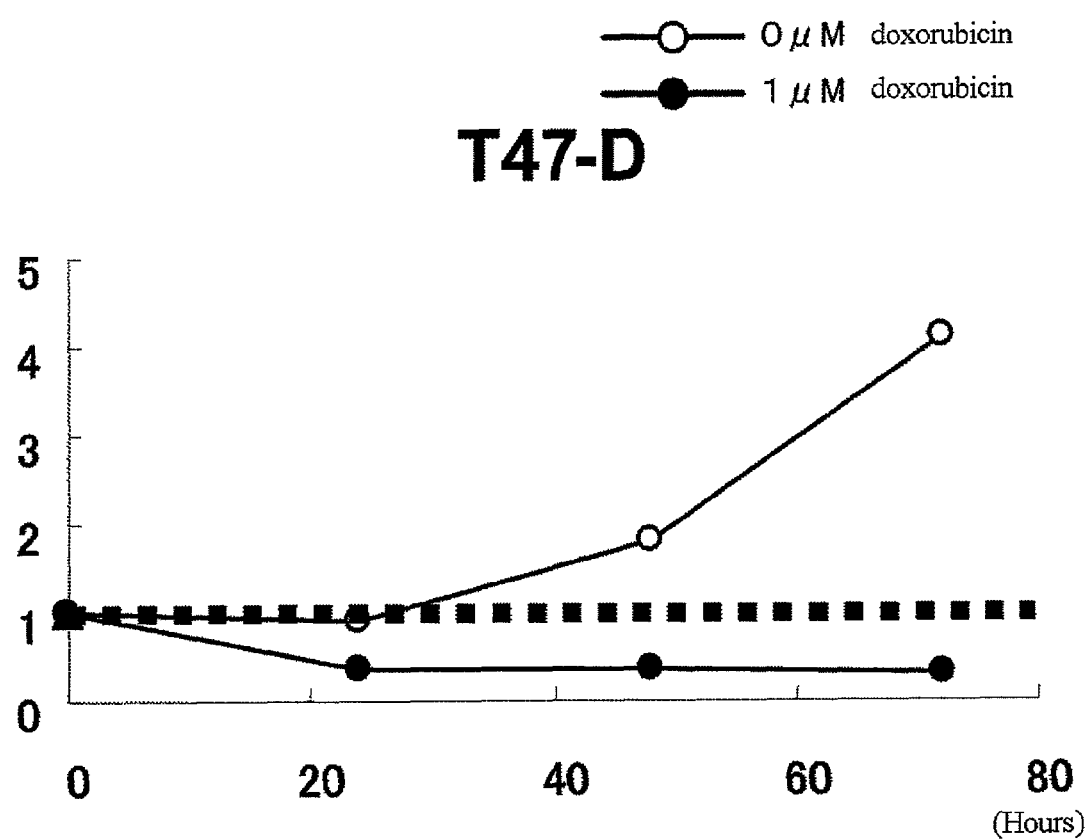
FIG. 4 shows the results of a cell growth test of T47-D in the presence or absence of doxorubicin.
Figure 5:
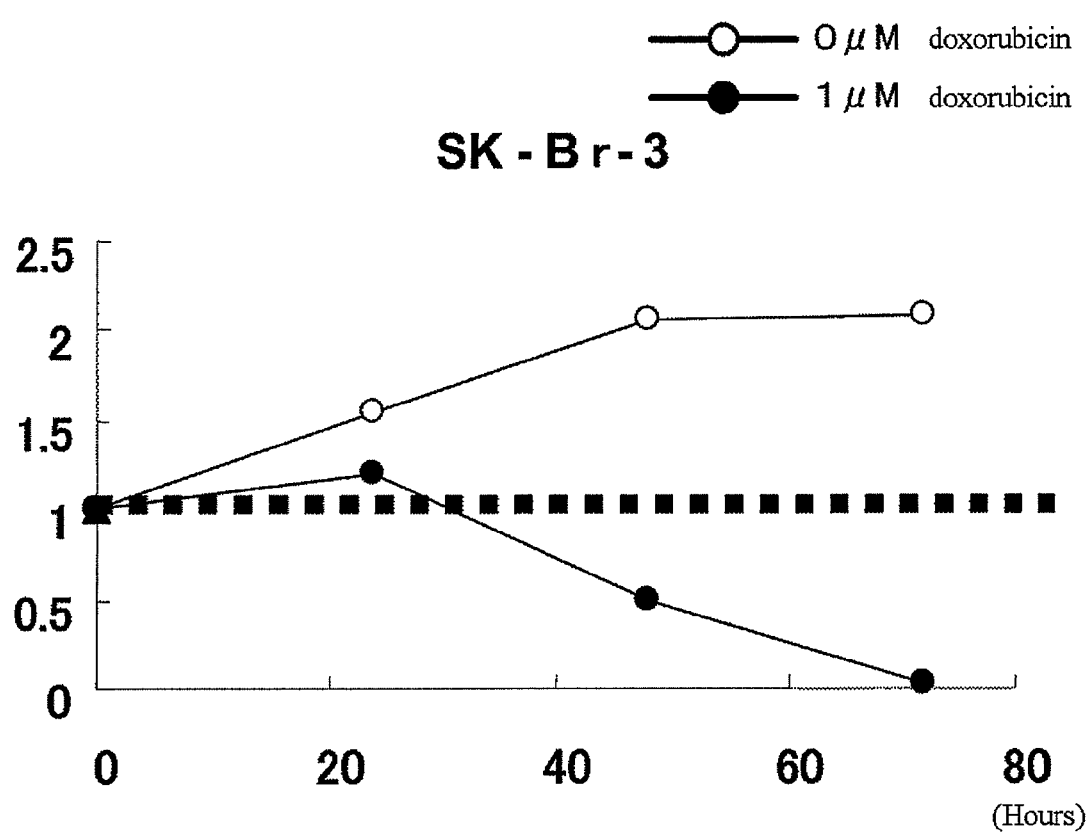
FIG. 5 shows the results of a cell growth test of SK-Br-3 in the presence or absence of doxorubicin.
Figure 6:
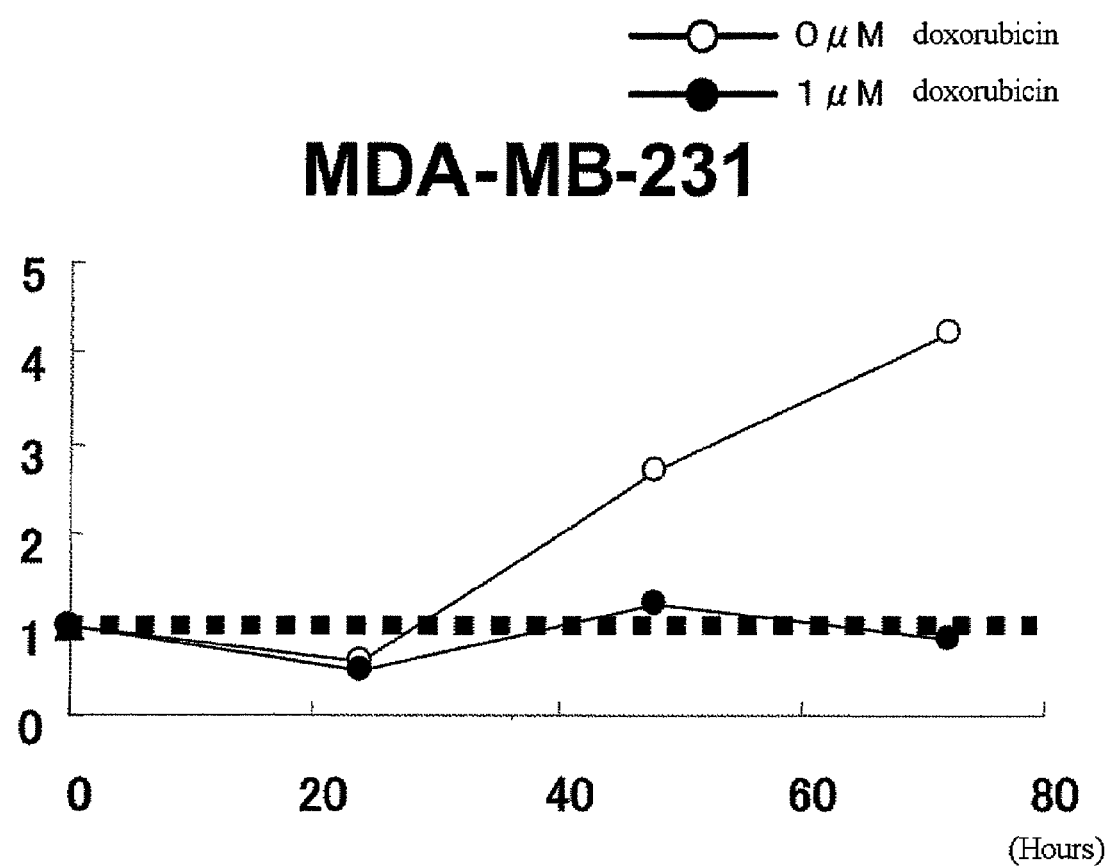
FIG. 6 shows the results of a cell growth test of MDA-MB-231 in the presence or absence of doxorubicin.

FIG. 2 is a flowchart showing the working of a program for executing determination of susceptibility to an anthracycline anticancer agent by the method for determining susceptibility to the anticancer agent. This program is stored in the memory 110d. First, the expression level of Akt in a cancer cell or cancer tissue as a sample, when entered by the input device 130, is sent by CPU 110a via the input-output interface 110f to RAM 110c where the data are memorized (step S1).

CPU 110a calls up a threshold value previously memorized as program data in the memory 110d. Comparison between the threshold value and the expression level of Akt is executed (step S2).

On the basis of the comparison result, CPU 110a then determines susceptibility to an anthracycline anticancer agent (step S3). CPU 110a determines that when the expression level of activated Akt is equal to or higher than the threshold value, the susceptibility to the anthracycline anticancer agent is "high". When the expression level of activated Akt is equal to or lower than the threshold value, the susceptibility to the anthracycline anticancer agent is determined to be "low".

Then, CPU 110a allows the above determination result to be stored in RAM 110c and simultaneously outputted to the display 120 via the image output interface 110h (step S4).

Although the expression level of activated Akt is entered by the input device 130 in this embodiment, this example is not limitative. For example, the expression level of activated Akt may be automatically obtained via the input-output interface 110f from a measurement device 200.

According to the method for determining susceptibility to an anticancer agent in the present invention, the efficacy of an anthracycline anticancer agent to a patent can be determined. Specifically, when the expression of activated Akt in a cancer cell or cancer tissue collected from a patient is high, the efficacy of the anthracycline anticancer agent to the patient can be determined to be high. On the other hand, when the expression of activated Akt is low, the efficacy of the anthracycline anticancer agent to the patient can be determined to be low.

The efficacy of an anthracycline anticancer agent to a patient can be determined more accurately by combining the detection of expression of HER-2 and/or PTEN, with the detection of activated Akt. For example, when the expression of activated Akt in a cancer cell or cancer tissue collected from a patient is high and simultaneously the expression of HER-2 and/or PTEN therein is high, the efficacy of the anthracycline anticancer agent to the patient can be more accurately determined to be high. On the other hand, when the expression of activated Akt in a cancer cell or cancer tissue collected from a patient is low and simultaneously the expression of HER-2 and/or PTEN therein is low, the efficacy of the anthracycline anticancer agent to the patient can be more accurately determined to be low.

By determining the efficacy of an anthracycline anticancer agent to a patient, administration of an effective anthracycline anticancer agent to the patient is made feasible. For a patient for whom the efficacy is determined to be low, an anticancer agent other than the anthracycline anticancer agent can be administered. Inefficient therapy can thereby be avoided. Further, the side-effect burden on the patient can be reduced.

EXAMPLES

Example 1

Preparation of Human Breast Cancer Cells and Cancer Tissues

Human breast cancer cells MCF-7, T47-D, SK-B-3, SK-Br-3, MDA-MB-231 and MDA-MB-468 were purchased from American Type Culture Collection (ATCC). 38 cancer cell samples (Nos. 1 to 38) were excised from 38 breast cancer patients with invasive breast cancer classified in stages I to IIIb according to the breast cancer stage classification. The 38 breast cancer patients are those who after removal of cancer tissue, received chemotherapy consisting essentially of administration of anthracycline anticancer agents. Each human breast cancer cell or cancer tissue was proliferated in Eagle's modified minimum essential medium (GIBCO) (hereinafter referred to merely as medium) containing 10% FCS (Commonwealth Laboratories), 1% (v/v) nonessential amino acid (GIBCO), 2 mM L-glutamine (Sigma Chemical), 100 µg/ml streptomycin (GIBCO), 100 U/ml penicillin (GIBCO) and 0.28 µg/ml fungizone (Squib Pharmaceuticals) in a humidified atmosphere of 5% $CO_2$/95% air at 37° C.

Example 2

Cell Growth Test $3.0 \times 10^3$ human breast cancer cells or cancer tissue were inoculated onto a medium in a 96-well plate and cultured for 1 day in a humidified atmosphere of 5% $CO_2$/95% air at 37° C. Thereafter, the medium was exchanged with a medium with or without 1 µM doxorubicin. Cell proliferation after 0, 24, 48 and 72 hours was measured by using a cell proliferation assay kit (Nippon Chemi-Con Corporation) or Cell Titer-Glo Luminescent Cell Viability assay (Promega) in accordance with its manufacturer's instructions. The results are shown in FIGS. 3 to 11.

Cell proliferation of MCF-7 (FIG. 3) and MDA-MB-231 (FIGS. 6 and 11), as compared with the control, was suppressed for 0 to 72 hours after administration of doxorubicin. However, the living cells are hardly changed or are increased from 0 hour after administration. That is, it is evidently demonstrated that the induction of apotosis of MCF-7 and MDA-MB-231 by doxorubicin is very low.

Figure 7:
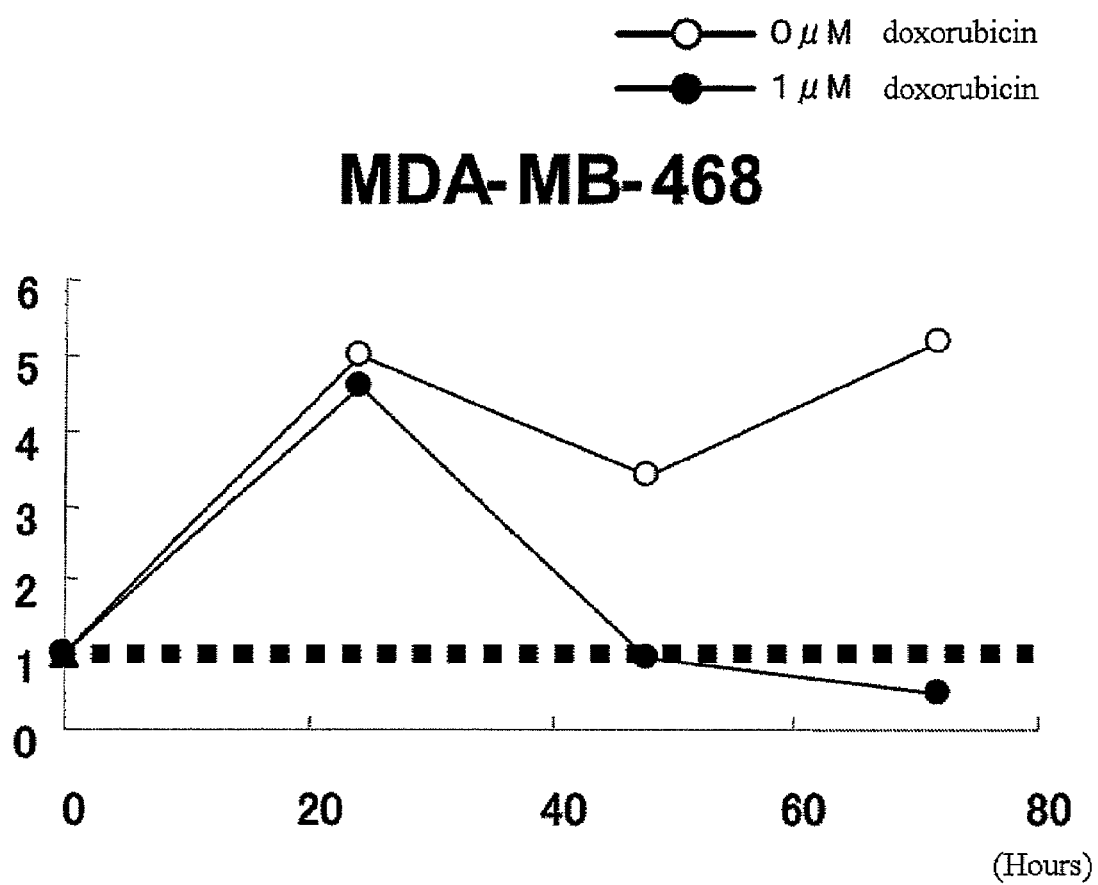
FIG. 7 shows the results of a cell growth test of MDA-MB-468 in the presence or absence of doxorubicin.
Figure 8:
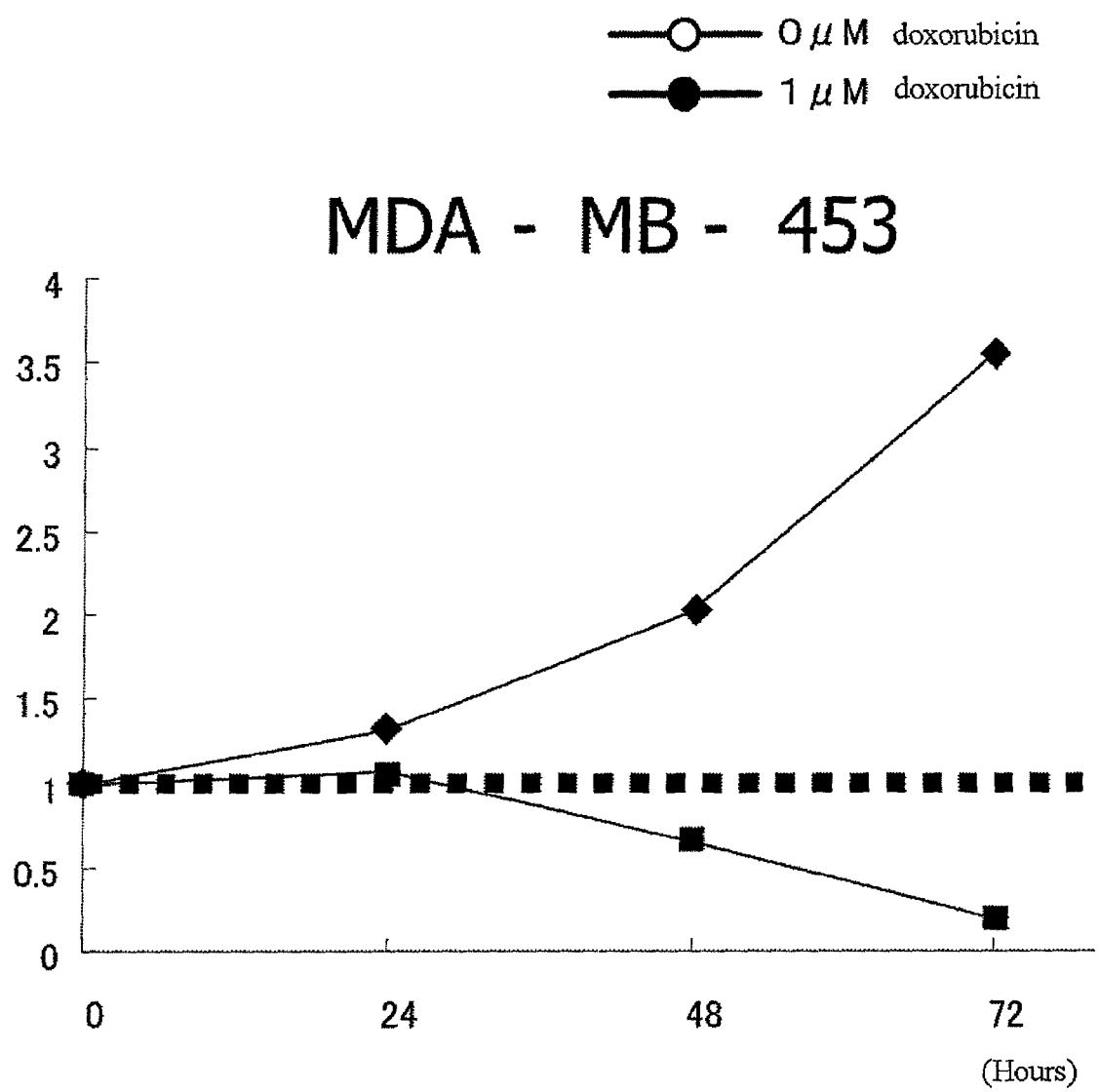
FIG. 8 shows the results of a cell growth test of MDA-MB-453 in the presence or absence of doxorubicin.

The living cells of T47-D (FIG. 4), SK-Br-3 (FIGS. 5 and 10), MDA-MB-468 (FIGS. 7 and 9) and MDA-MB-453 (FIG. 8) are gradually decreased with time from 0 hour after administration of doxorubicin. That is, it can be seen that the apotosis of T47-D, SK-Br-3, MDA-MB-468 and MDA-MB-453 was induced by doxorubicin. Here, the induction of apotosis of SK-Br-3 (FIGS. 5 and 10) and MDA-MB-453 (FIG. 8) by administration of doxorubicin is so high that the living cells hardly remain after 72 hours. On the other hand, the apotosis of T47-D (FIG. 4) and MDA-MB-468 (FIGS. 7 and 9) was induced, but the effect thereon can be seen to be lower than on SK-Br-3 (FIGS. 5 and 10) and MDA-MB-453 (FIG. 8).

Example 3

Detection, by Western Blotting, of Expression of Activated Akt, HER-2 and PTEN in Human Breast Cancer Cells or Cancer Tissue $1.0 \times 10^6$ human breast cancer cells or cancer tissue were inoculated onto a medium in a 60-mm culture dish and cultured for 1 day. A culture and human breast cancer cells or cancer tissue adhering to each culture dish were recovered with a cell scraper and centrifuged at 190×g at 4° C. for 5 minutes to remove the culture medium. Then, the remaining cell mass was frozen in liquid nitrogen and stored overnight at −80° C. 100 µl of a cell lysing solution (0.1% NP-40, 50 mM Tris-HCl pH7.5, 5 mM EDTA, 50 mM NaF, 1 mM $Na_3VO_4$, 0.2% protease inhibitor cocktail (Sigma)) was added to the frozen cell mass, to suspend the cells by pipetting, and then left for 10 minutes on ice. The suspension was centrifuged at 12000×g, 4° C., for 10 minutes, and the supernatant was transferred as a sample to a new microtube, and an aliquot thereof was used to determine its protein content by the Lowry method.

A 6×SDS sample buffer was added to the sample which was then heated at 100° C. for 5 minutes, thereby denaturing the protein in the sample. The sample was centrifuged at 12000×g, 4° C., for 20 seconds, and the supernatant was transferred to a new microtube. The sample was added in an amount of 20 mg protein/well to SDS-PAGE gel (Daiichi Pure Chemicals Co., Ltd.) and then subjected to electrophoresis under the conditions of 2 hours and 20 mA. Using Mini Trans-Blot cell (BioRad), the protein was transferred from the SDS-PAGE gel to Immobilon FL membrane (hereinafter referred to simply as membrane) (Millipore) under the conditions of 100V, 2 hours and 4° C. Then, the membrane was incubated for 30 minutes at normal temperature in TBS-T buffer containing 4% BSA (10 mM Tris-HCl, pH 7.6, 150 mM NaCl, 0.1% (v/v) Tween 20). Then, the membrane was incubated overnight at 4° C. in TBS-T buffer containing 1% BSA having the following diluted primary antibodies.

(Primary Antibodies)

Phospho-Akt (Ser473) (587F11) Mouse mAb (Cell Signaling Technologies), 1/1000

Akt Antibody (Cell Signaling Technologies), 1/1000

PARP Antibody (Cell Signaling Technologies), 1/1000

Anti-Glyceramidehyde-3-Phosphate Dehydrogenase Rabbit Polyclonal Antibody (GAPDH) (TREVIGEN), 1/1000

Anti-PTEN (A2B1) antibody (Santa Cruz Biotechnology), 1/200

Anti-PI3-kinase p85a (Z-8) (Santa Cruz Biotechnology), 1/200

Anti-HER2 antibody (Upstate), 1/1000

The membrane which had been incubated overnight was washed by being incubated 3 times at normal temperature for 5 minutes in TBS-T buffer. After washing, the membrane was incubated at normal temperature for 1 hour in TBS-T buffer containing 1% BSA having the following diluted secondary antibodies, thereby reacting with the secondary antibodies.

(Secondary Antibodies)

Polyclonal rabbit anti-mouse polyclonal immunoglobulins/HRP (Dako), 1/2000

Polyclonal swine anti-rabbit polyclonal immunoglobulins/HRP (Dako), 1/2000

After reaction with the secondary antibodies, the membrane was washed again 3 times with TBS-T buffer and treated with ECL Plus (Amersham). The results are shown in FIGS. 12 and 13.

Figure 12:
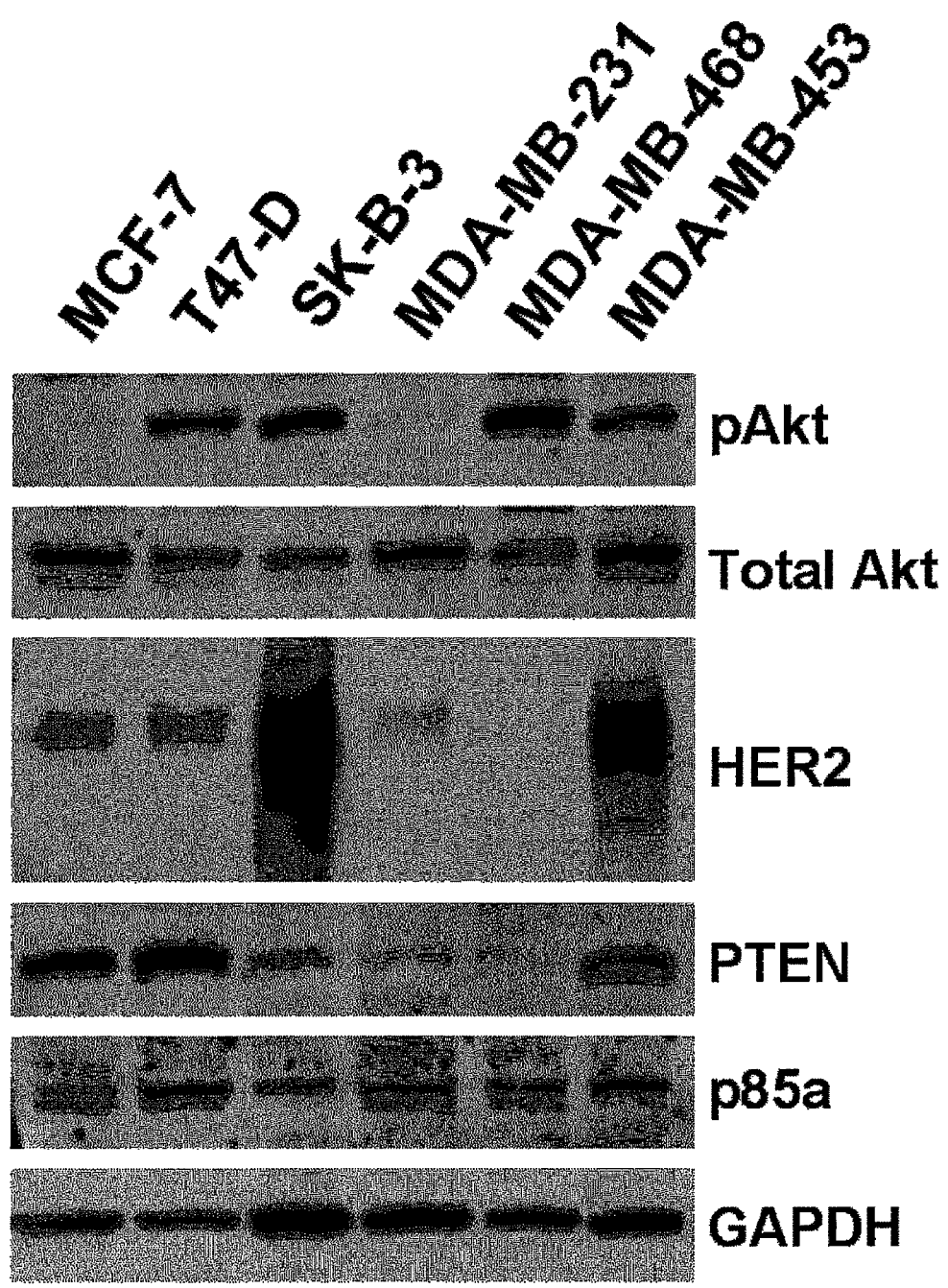
FIG. 12 shows the results of confirmation, by western blotting, of expression of activated Akt, HER-2 and PTEN in MDA-MB-453, MDA-MB-468, MDA-MB-231, SK-B-3, T47-D and MCF-7.

As is evident from FIG. 12, it can be seen that the expression of phosphorylated Akt, that is, activated Akt, is very low in MCF-7 (FIG. 3) and MDA-MB-231 (FIGS. 6 and 11) whose induction of apotosis by doxorubicin was very low. On the other hand, the expression of activated Akt can be evidently detected as a band in T47-D (FIG. 4), SK-Br-3 (FIGS. 5 and 10), MDA-MB-468 (FIGS. 7 and 9) and MDA-MB-453 (FIG. 8) whose apotosis was induced by doxorubicin.

Figure 9:
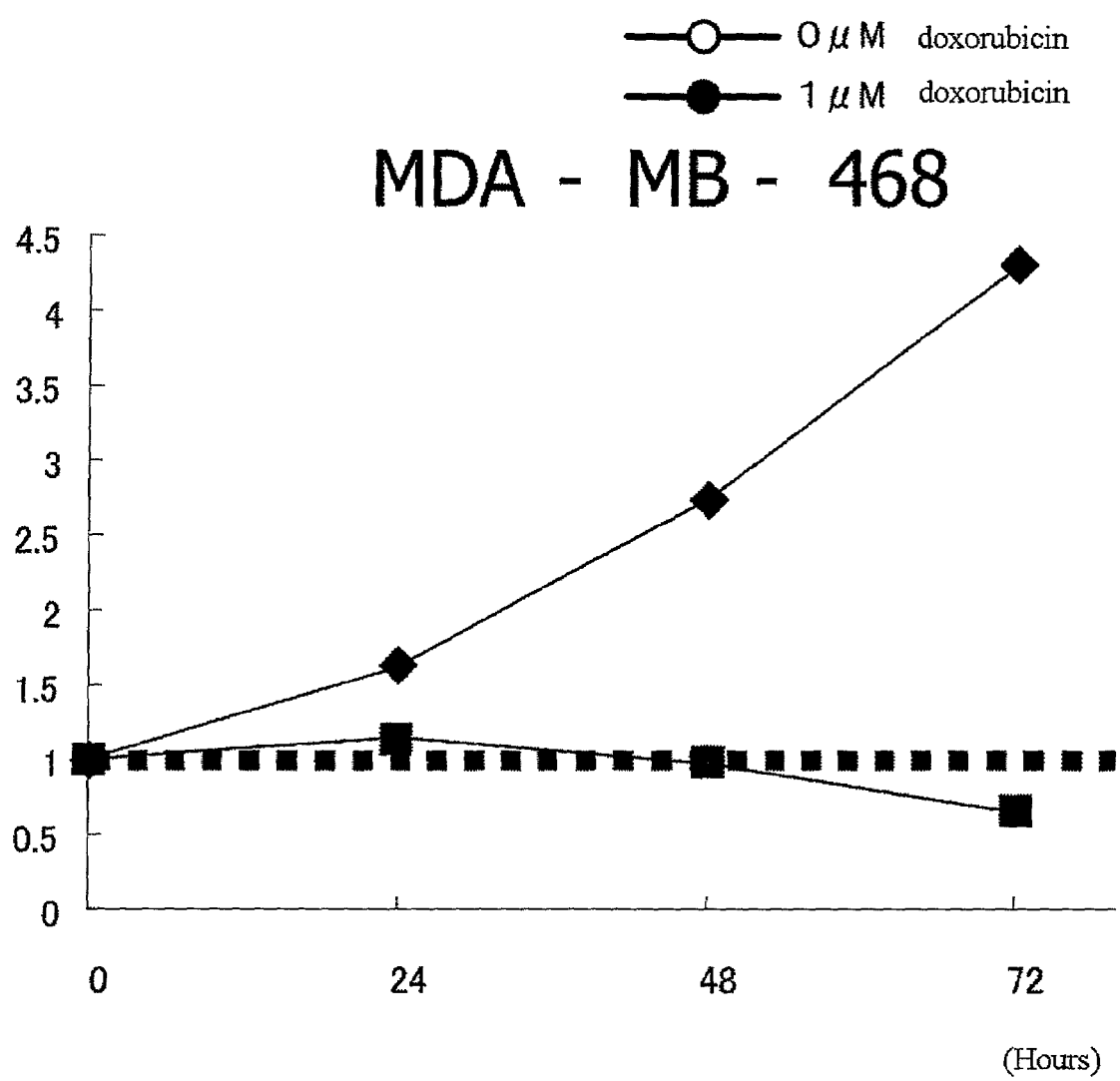
FIG. 9 shows the results of a cell growth test of MDA-MB-468 in the presence or absence of doxorubicin.
Figure 10:
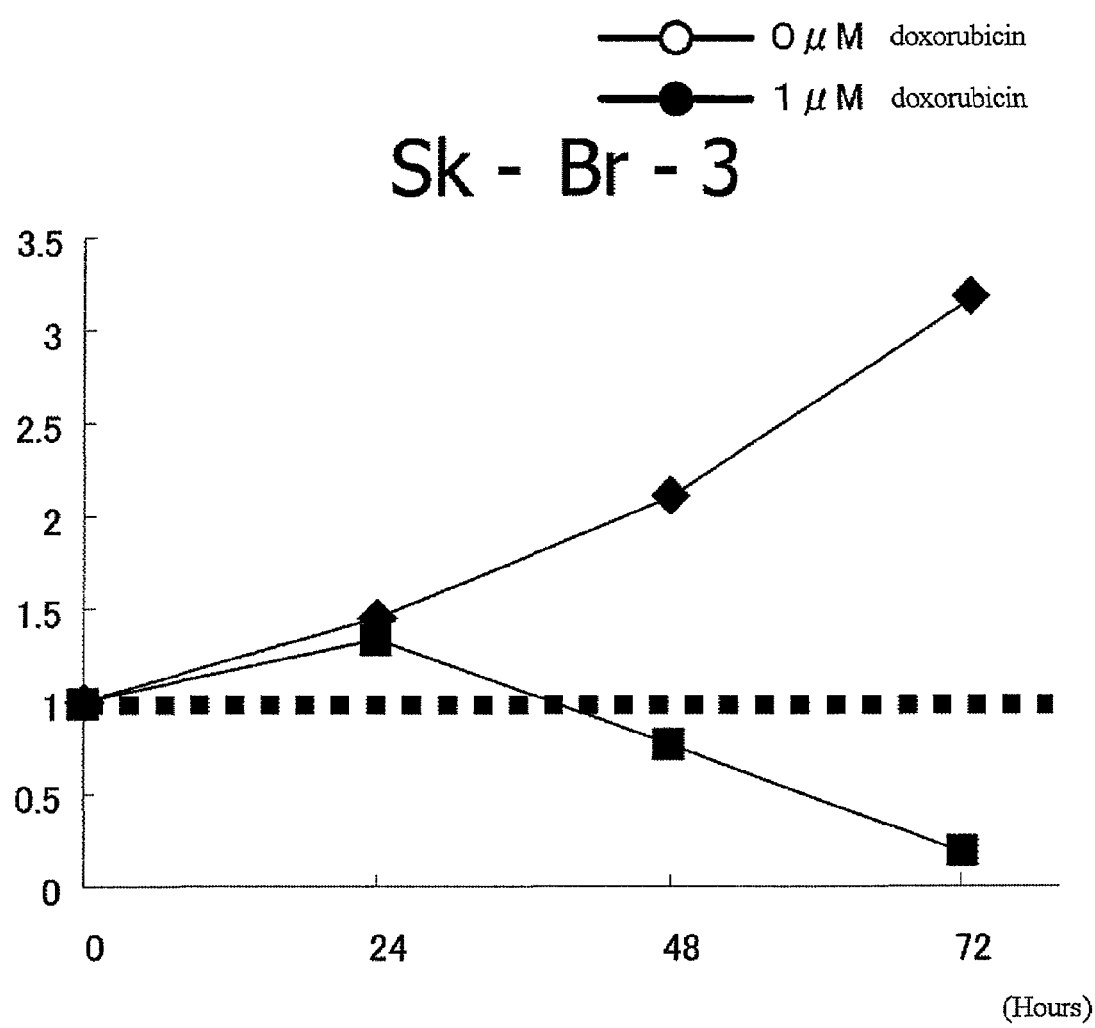
FIG. 10 shows the results of a cell growth test of SK-Br-3 in the presence or absence of doxorubicin.
Figure 11:
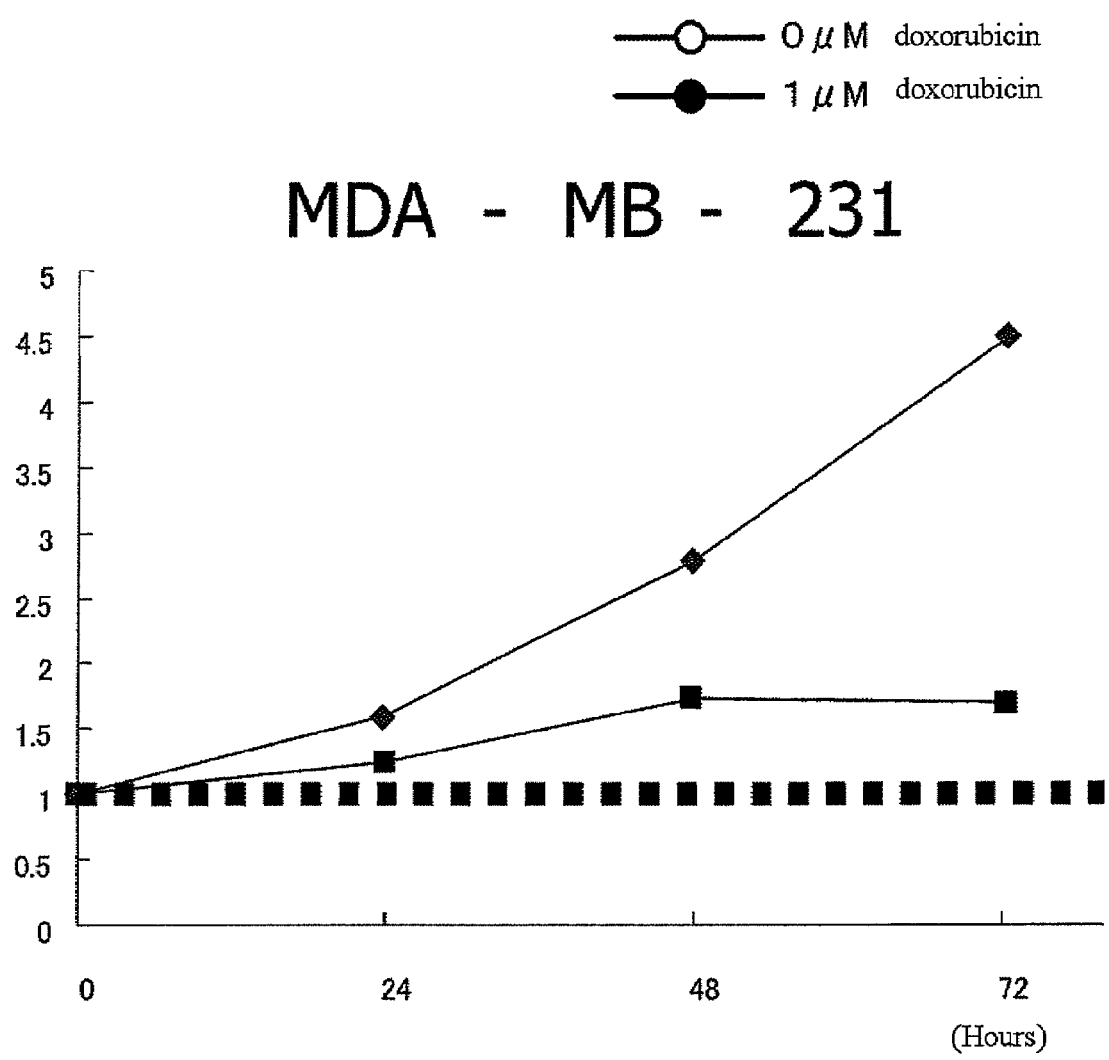
FIG. 11 shows the results of a cell growth test of MDA-MB-231 in the presence or absence of doxorubicin.

Here, the expression of activated Akt can be confirmed in T47-D (FIG. 4) and MDA-MB-468 (FIGS. 7 and 9) whose induction effect of apotosis by doxorubicin was low. However, it can be seen that the expression of HER-2 is evidently lower in T47-D and MDA-MB-468 than in SK-Br-3 (FIGS. 5 and 10) and MDA-MB-453 (FIG. 8) whose induction effect of apotosis by doxorubicin was high. It can also be confirmed that the expression level of PTEN is low in MDA-MB-468 (FIGS. 7 and 9).

Figure 13:
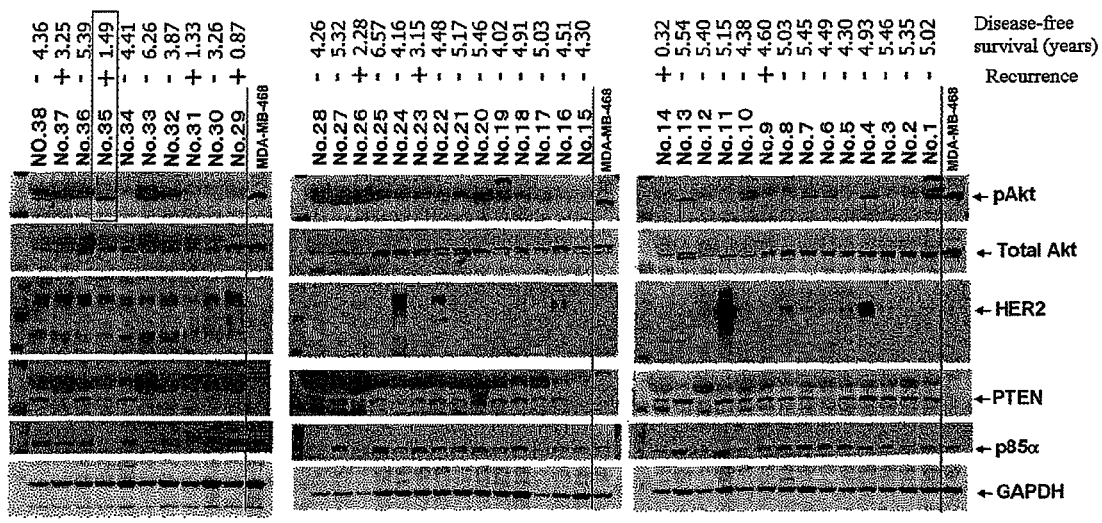
FIG. 13 shows the results of confirmation, by western blotting, of expression of activated Akt, HER-2 and PTEN in 38 samples of cancer cells and cancer tissues from breast cancer patients who were treated mainly with anthracycline anticancer agents.

FIG. 13 shows the results of western blotting of the 38 samples that are cancer tissues from breast cancer patients treated mainly with anthracycline anticancer agents. In FIG. 13, disease-free survival (years) shows the number of years having elapsed without recurrence of cancer in a patient after the treatment. The symbols "+" and "−" in the item recurrence indicate the presence and absence of recurrence, respectively; that is, "+" indicates a patient with recurrence, and "−" indicates a patient without recurrence. For example, No. 1 refers to a patient with an elapse of 5.02 years without recurrence of cancer after the treatment, and No. 9 refers to a patient with recurrence of cancer after an elapse of 4.60 years after the treatment.

With respect to 8 samples with recurrence of cancer (No. 9, No. 14, No. 23, No. 26, No. 29, No. 31, No. 35 and No. 37), the expression of activated Akt is evidently low in all the samples except for No. 35. The expression levels of HER-2 and PTEN are low in No. 35 wherein the cancer recurred in spite of the occurrence of expression of activated Akt. Particularly, the expression level of PTEN is extremely low in No. 35.

Example 4

Measurement of Expression Level of Activated Akt

Bands of phosphorylated and non-phosphorylated Akt in human breast cancer cells and cancer tissues, obtained by the western blotting described above, were measured for their signal count. In this measurement, Molecular Imager FX (BioRad) was used. The Akt activity was expressed in terms of the ratio of the signal count of phosphorylated Akt to the signal count of phosphorylated and non-phosphorylated Akt. The measurement results are shown in FIGS. 14 and 15.

Figure 14:
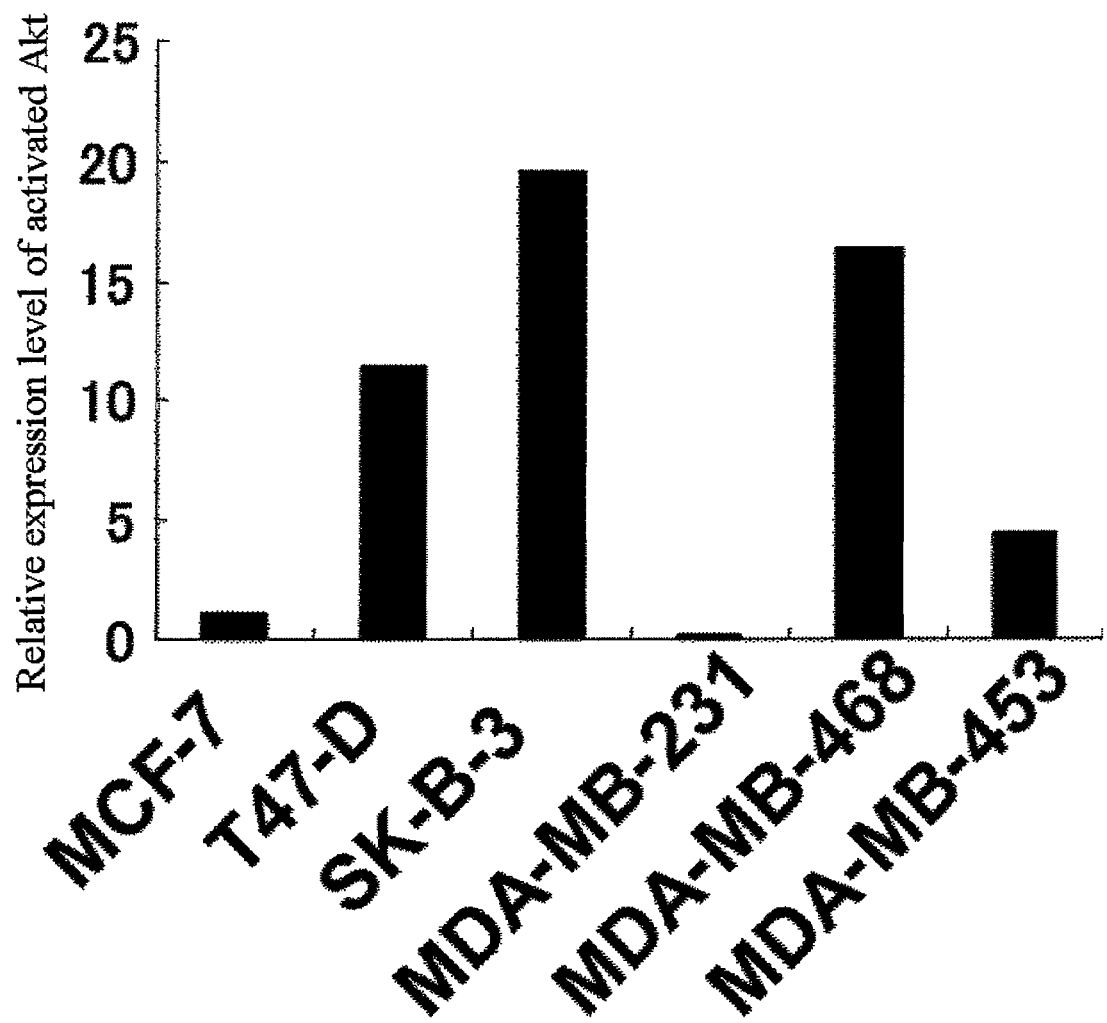
FIG. 14 shows the analytical results of signal counting of phosphorylated Akt in MDA-MB-453, MDA-MB-468, MDA-MB-231, SK-B-3, T47-D and MCF-7.

As is evident from FIG. 14, the expression level of activated Akt is extremely low in T47-D and MDA-MB-468 whose induction effect of apotosis by doxorubicin was extremely low, among the human cancer cells or cancer tissues MCF-7, T47-D, SK-B-3, SK-Br-3, MDA-MB-231 and MDA-MB-468.

Figure 15:
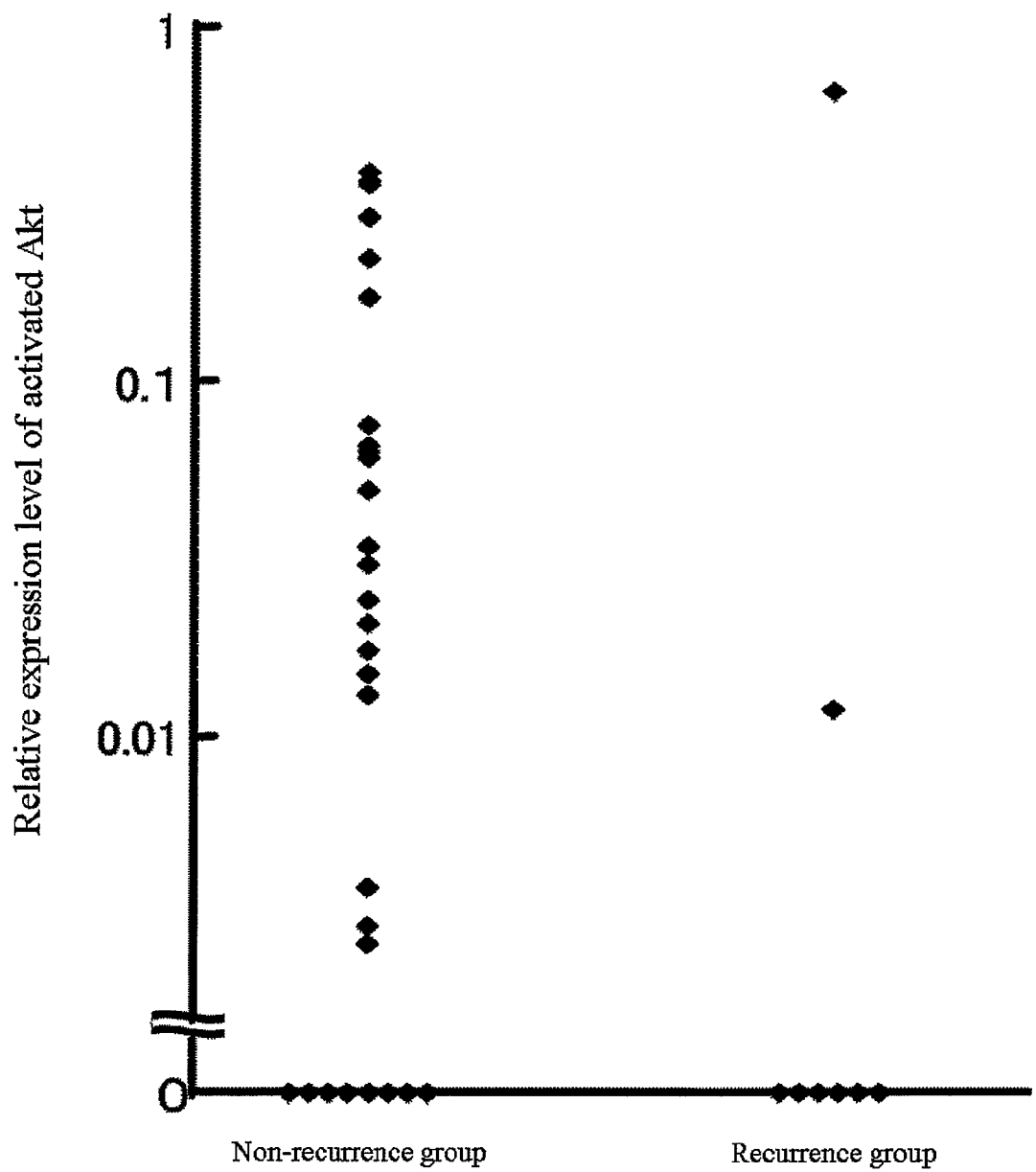
FIG. 15 shows the analytical results of signal counting of phosphorylated Akt in 38 samples of cancer cells and cancer tissues from breast cancer patients with or without relapse who were treated mainly with anthracycline anticancer agents.

FIG. 15 shows the expression levels of activated Akt in a cancer recurrence group and a non-recurrence group into which the 38 samples of cancer tissues from breast cancer patients treated mainly with anthracycline anticancer agents are divided.

FIG. 15 reveals that in the non-recurrence group, there are many breast cancer patients with overexpression of activated Akt, while in the recurrence group, there are many breast cancer patients with underexpression of activated Akt.

As is evident from the foregoing examples, an anthracycline anticancer agent is highly effective in treatment of cancer cells or cancer tissues with overexpression of activated Akt, wherein adverse prognosis is regarded as highly likely to occur. On the other hand, an anthracycline anticancer agent is low effective in treatment of cancer cells or cancer tissues with underexpression of activated Akt. An anthracycline anticancer agent is effective for cancer cells or cancer tissues wherein activated Akt is highly expressed and simultaneously HER-2 and/or PTEN is highly expressed.

That is, the degree of efficacy of an anthracycline anticancer agent can be determined by detecting activated Akt in cancer cells or cancer tissues from individual cancer patients. Accordingly, selection of an effective anticancer agent is made feasible. Particularly, whether selection of an anthracycline anticancer agent is suitable or not can be determined more accurately. Therefore, inefficient treatment of a patient can be avoided. In addition, a disadvantage of side effects can be reduced. As a result, patient's QOL can be improved.

The foregoing detailed description and examples have been provided by way of explanation and illustration, and are not intended to limit the scope of the appended claims. Many variations in the presently preferred embodiments will be obvious to one of ordinary skill in the art, and remain within the scope of the appended claims and their equivalents.

What is claimed is:

1. A method for determining an efficacy of an anthracycline anticancer agent to a patient, comprising steps of:
   determining a level of expression of activated Akt in a cancer cell or a cancer tissue extracted from the patient;
   correlating the level of expression with efficacy, wherein when the expression is above a threshold level, the anthracycline anticancer agent is effective.

2. The method according to claim 1, wherein the cancer cell or the cancer tissue is a cell or a tissue of lung cancer, stomach cancer, colon cancer, ovarian cancer, brain cancer, breast cancer, prostate cancer, skin cancer or leukemia.

3. The method according to claim 1, wherein the anthracycline anticancer agent is daunorubicin, doxorubicin, pirarubicin, aclarubicin, epirubicin, oxaunomycin or idarubicin.

4. The method according to claim 1 further comprises a step of determining an expression level of human epidermal growth factor receptor 2 (HER-2) in the cancer cell or the cancer tissue extracted from a patient.

5. The method according to claim 4, wherein the determining step is performed so as to determine that
   the anthracycline anticancer agent is extremely effective according to a predetermined correlation of expression levels of activated Akt, expression levels of HER-2 when the detected expression levels of the activated Akt and the HER-2 are above each of their respective threshold levels.

6. The method according to claim 1, further comprises a step of determining an expression level of Phosphatase and Tensin Homolog Deleted from Chromosome 10 (PTEN) in the cancer cell or the cancer tissue extracted from a patient.

7. The method according to claim 6, wherein the determining step is performed so as to determine that
   the anthracycline anticancer agent is extremely effective according to a predetermined correlation of expression levels of activated Akt, expression levels of PTEN when the detected expression levels of the activated Akt and the PTEN are above each of their respective threshold levels.

* * * * *